US005081115A

United States Patent [19]

Vreman et al.

[11] Patent Number: 5,081,115

[45] Date of Patent: Jan. 14, 1992

[54] METHOD TO PREVENT NEONATAL JAUNDICE WITH METALLOPORPHYRIN COMPOSITIONS

[75] Inventors: Hendrik J. Vreman, Los Altos; David K. Stevenson, Palo Alto, both of Calif.

[73] Assignee: The Board of Trustees of the Leland Stanford Junior University, Stanford, Calif.

[21] Appl. No.: 328,205

[22] Filed: Mar. 24, 1989

Related U.S. Application Data

[63] Continuation-in-part of Ser. No. 108,743, Oct. 15, 1987, Pat. No. 4,831,024.

[51] Int. Cl.[5] .................. A61K 31/555; C07D 487/22

[52] U.S. Cl. .................................... 514/185; 540/145

[58] Field of Search ......................... 540/145; 514/185

[56] References Cited

U.S. PATENT DOCUMENTS 4,734,360 3/1988 Phillips ................................ 435/188

4,831,024 5/1989 Vreman et al. ..................... 514/185

OTHER PUBLICATIONS

J. E. Falk, *Porphyrins and Metalloporphyrins*, Elsevier Pub. Co. (1964), pp. 118–119.

Chem. Abstract 104:95482m, (1986); Attached English Abstract; both for JP 60,190,711, 28 Sep. 1985.

Drummond et al., *Science* (1982) 217:1250–1252.

Hamori et al., *Res. Commun. Chem. Pathol. Pharmacol.* (1988) 62:41–48.

McDonagh, J., *Photochem. Photobiol.* (1987) 1:127–133.

Ostrander et al., *J. Lab. Clin. Med.* (1982) 100(5):745–755.

Qato et al., *Biochem. J.* (1985) 266:51–57.

San Francisco Chronicle (27 May 1989) "Patent File".

New York Times (12 Apr. 1988) "Science".

Smith et al., *J. Pediatric Gastroenterology and Nutrition* (1984) 3:77–80.

Smith et al., *Pediatrics* (1985) 75(2):278–280.

Stevenson et al., *Biology of the Neonate* (submitted for publication Dec. 14, 1988).

Stevenson et al., *Amer. J. Dis. Children* (in press at time of application).

Stevenson et al., *J. Lab. Clin. Med.* (Oct., 1979) pp. 649–654.

Stevenson et al., *Pediatrics* (1988) 81:881–882.

Scott et al., *Photochem. Photobiol.* (1988) 27:78S.

Vreman et al., *Pediatric Res.* (1989) 26:362–5.

Vreman et al., *Clin. Chem.* (1987) 33:694–697.

Verman et al., *J. Chromatog.* (1988) pp. 1–5.

Hamori et al., *J. Pediatric Gastroenterology and Nutrition* (1989) 8:110–115.

Stevenson et al., *AJDC* (1989) 143:353–356.

Vreman et al., *Biochem. Biophys. Res. Comm.* (1987) 148(1):417–421.

Delaney, A. et al., *Pediatrics* (1988) 81:498–504 Photophysical Properties of Sn Porphyrins: Potential Clinical Inplications.

Drummond, G. S. et al., *Arch Biochem Biophys* (1987) 255:64–74 Reduction of the $C_2$ and $C_4$ Vinyl Groups of Sn Photoporphyrin . . . .

*Primary Examiner*—Nicholas S. Rizzo
*Assistant Examiner*—Philip Datlow
*Attorney, Agent, or Firm*—Morrison & Foerster

[57] ABSTRACT

A formulation for administration of a metalloporphyrin compound useful in the treatment or prevention of jaundice is described. The formulation comprises the metalloporphyrin in admixture with an excipient which is a water-soluble organic amine, said composition having been neutralized to neutral pH. The formulation may advantageously contain a stabilizer, such as human serum albumin.

16 Claims, No Drawings

METHOD TO PREVENT NEONATAL JAUNDICE WITH METALLOPORPHYRIN COMPOSITIONS

This is a continuation-in-part of U.S. patent application Ser. No. 108,743, filed 15 Oct. 1987, now U.S. Pat. No. 4,831,024.

TECHNICAL FIELD

The invention relates to the field of clinical medicine and epidemiology. More specifically, the invention concerns a method to screen human subjects for incipient hyperbilirubinemia and to prevent jaundice in subjects at risk.

BACKGROUND ART

Infant jaundice, or hyperbilirubinemia, is a significant clinical problem, occurring in about 5% of full-term infants. The syndrome is the direct result of increased bilirubin levels in the infant body. Adults also have problems with jaundice, but they are generally not as serious or as widespread because most adults are capable of conjugating excess bilirubin with sugars and clearing this toxin from the body. This detoxification mechanism is not fully developed in neonates. Nevertheless, some adults, such as those who have hepatitis or obstructions to bile flow, are subject to jaundice as well.

Various treatments have been suggested for both infant and adult jaundice when these problems occur. These treatments include phototherapy, exchange transfusions, extracorporeal filtration systems, and drugs which induce an efficient clearance system. None of these treatments is simple to administer or effective without negative side reactions, including risk of injury or death. If the jaundice is not promptly treated, serious damage to the nervous system can result, especially in infants, as the elevated amounts of bilirubin act as a neurotoxin, and the blood/brain barrier in infants is incompletely developed. Also, the foregoing treatments are administered after the fact—i.e., after the jaundice has already appeared.

In neonates, the visible signs of the disorder manifest themselves usually at about 72 hours after birth, often after the infant has left the hospital or birth center. Thus, the signs may appear when the baby is no longer under the observation of trained medical personnel. In order to minimize the organic and neurological damage caused by the elevated bilirubin levels, therefore, it is advantageous to intervene before control over treatment has been lost, which is often before the signs actually appear.

One aspect of effective intervention is the identification of individuals at risk for developing this syndrome. Because, in order to eliminate as totally as possible the incidence of neonatal jaundice, every infant must be tested, effective prediction requires a simple, noninvasive procedure. Measurement of bilirubin in the blood per se is not a satisfactory approach because accurate prediction of a potential to develop jaundice rests on detection of increased bilirubin production, as opposed to the levels of bilirubin in the blood. Blood bilirubin levels are influenced not only by production, of course, but also by rates of excretion, and hepatic and intestinal uptake.

The parent application herein discloses and claims a protocol for effective prevention of the occurrence of neonatal jaundice in an infant population. The disclosure of this application, now issued as U.S. Pat. No. 4,831,024 is incorporated herein by reference. The disclosed method involves testing each member of the infant population for high levels of carbon monoxide exhalation, and treating those members of the population perceived to be at risk with a zinc porphyrin derivative, preferably zinc mesoporphyrin or zinc protoporphyrin. Only generalized directions for the formulation of the zinc porphyrin drug are disclosed.

In addition to the use of zinc porphyrin derivatives in the treatment of jaundice, both in neonates and in adults, other groups have suggested the use of alternative metalloporphyrins, including tin, chromium and manganese porphyrin derivatives. While it is believed that the overall result from the use of zinc analogs is most desirable, other workers may prefer to use these other metallo derivatives.

In all cases, formulation has been difficult because of the insolubility of the relevant metalloporphyrin in water, even in the presence of mineral base. Administration of any of these compounds is greatly enhanced by a formulation which permits suitably high concentrations to be achieved.

DISCLOSURE OF THE INVENTION

The invention provides a formulation for metalloporphyrins used in the treatment and/or prevention of neonatal and/or adult jaundice. Thus, in one aspect, the invention is directed to pharmaceutical compositions useful in administering effective amounts of metalloporphyrins at relatively high concentration levels, which compositions comprise an effective amount of metalloporphyrin derivative in admixture with a water-soluble organic amine base, said composition neutralized to pH 7.4–7.8 with a compatible organic or inorganic acid. The organic amine base excipient is used in an aqueous solution and, in order to prepare the composition, the active ingredient is first dissolved in the aqueous solution of amine, and subsequently neutralized.

In a second aspect, the invention is directed to a method to prepare a composition effective in treating or preventing a neonatal or other jaundice conditions which method comprises dissolving an effective amount of a metalloporphyrin in an aqueous solution of a water-soluble organic amine followed by neutralizing the resulting solution to a pH of 7.4–7.8.

Optionally, other excipients may also be added.

MODES OF CARRYING OUT THE INVENTION

The invention provides formulations of metalloporphyrins, which metalloporphyrins are effective in the treatment of jaundice. A number of these porphyrins have been suggested in the art, including complexes of the porphyrin nucleus with tin, zinc, manganese, nickel and chromium ions. The nature of the porphyrin nucleus can also be varied.

By "metalloporphyrin" derivatives is meant complexes of metal ion with various porphyrin-related materials, such as porphyrins containing alternate sidechains to those contained in protoporphyrin or mesoporphyrin, as well as chlorins and phlorins. These latter classes differ from the porphyrins only by the degree of hydrogenation of the tetrapyrole nucleus. Thus, included within the scope of the invention are metal ion compounds of the general formula

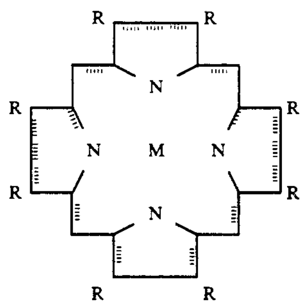

wherein

"M" is selected from the group consisting of $Zn^{+2}$, $Sn^{+4}$, $Mn^{+2}$, $Ni^{+2}$ and $Cr^{+3}$;

each R is independently selected from the group consisting of H and lower alkyl or alkenyl (1-6C) optionally containing one or more functional groups; and the dotted lines in the organic moiety represent the presence or absence of a pi-bond at the indicated location.

Preferred embodiments of R are H, ethyl, 1-hydroxyethyl, vinyl, methyl and 2-carboxyethyl.

(When a pi-bond is absent, at the C to which "R" is attached, there are, of course, two independently selected Rs present.)

For example, in protoporphyrin-IX, all of the dotted lines represent pi-bonds and the designated R groups are, reading clockwise from the top, methyl, vinyl, methyl, vinyl, methyl, 2-carboxyethyl, 2-carboxyethyl and methyl. In mesoporphyrin, the vinyl groups are reduced to ethyl. In etioporphyrin, these substituents are, reading clockwise, methyl, ethyl, methyl, ethyl, methyl, ethyl, ethyl, methyl. These analogs are merely illustrative, and a variety of metal-ion-containing porphyrin derivatives are commercially available. Preferred embodiments of the tetrapyrrole analogs are mesoporphyrin and protoporphyrin.

Preferred metal ions are chromium, manganese, tin and zinc, more preferably tin and zinc, and most preferably zinc. A number of such analogs are available commercially, for example, from Porphyrin Products, Inc., Logan, Utah.

A preferred method of evaluating the effects of various porphyrin derivatives on heme oxygenase activity in whole animals and in tissue samples permits convenient testing for efficacy of various types of derivatives. See, for example, Hamori, C. J., et al. "Zinc Protoporphyrin Inhibits Bilirubin Production in Adult Rats" *J. Pediatric Gastroenterology and Nutrition* (1987) (in press); Vreman, H. J. et al. "Direct Measurement of Heme Oxygenase Activity by Gas Chromatography" *Abstracts: American Pediatric Society and Society for Pediatric Research* (1987), Ser. No. 06,194 and *Anal Biochem* (1988) 168:31-38. By assessing the ability of a particular porphyrin derivative to suppress heme oxyqenase activity either in isolated tissues or in whole animals, its appropriateness as a chemopreventive in the method of the invention can be readily assessed.

A large number of publications report the results of tests designed to quantify the characteristics of zinc or tin protoporphyrin or mesoporphyrin derivatives in tests related to the efficacy and potential side effects of these drugs when used to treat jaundice. See, for example, Stevenson, D. K., et al. *Pediatrics* (1980) 81:881-882; Scott, J., et al. *Photochem Photobiol* (1988) 27:785; Hamori, C. J., et al. *Research Commun Chem Pathol Pharmacol* (1988) 62:41-48. It is known that while both the tin and zinc porphyrin derivatives in general, and the mesoporphyrin and protoporphyrin complexes of these metals in particular, are effective in the treatment of jaundice, the toxicity of the tin compounds is considerably higher and administration of the tin compounds results in photo-sensitivity in the subject. Hence, for these reasons, the zinc derivatives, which are nontoxic, are preferred.

The porphyrin derivatives are generally administered in a formulation suitable for injection subcutaneously, intramuscularly, intraperitoneally, or intravenously, preferably IV or IM. Oral administration may also be used. In the past, such injectable formulations were prepared by dissolving the drug in a solution or preparing a suspension in water where solubility was putatively enhanced by the addition of mineral bases such as sodium hydroxide or sodium phosphate ($Na_3PO_4$). In typical prior art preparations, the porphyrin derivative would be dissolved in a concentrated solution of the base, diluted, and then neutralized with an inorganic acid such as HCl. In one typical preparation, for example, 52 mg of hemin was dissolved in 0.5 ml 0.4M sodium phosphate and the volume adjusted to 8 ml with distilled water. Then, 400 mg bovine serum albumin (BSA) was added with vigorous stirring, and the pH was slowly adjusted to pH 7.4 with 1.0 N HCl. The total volume was then adjusted to 10 ml with distilled water. The resulting solution was thus roughly 0.5% in the drug. It should be noted, however, that not all of the active ingredients included within the invention are sufficiently soluble to have resulted in the concentration obtained for hemin. The tin porphyrin derivatives are less soluble than hemin, and the zinc porphyrin compounds are even less soluble.

In the formulations of the invention, a water-soluble organic amine is used to dissolve the drug, and the pH again is neutralized. Solubility is thus enhanced, and the excipient amine provides a milder base. Suitable water-soluble organic amines include ethylamine, diethylamine, triethylamine, ethanolamine, diethanolamine, and triethanolamine. All of these exemplary amines are miscible with water and are strong bases.

In general, the formulations are prepared by first dissolving the drug in an aqueous solution of the amine, wherein the concentration of the amine in water is 5-50%, preferably 10-20%. The initial solution can be made at relatively high concentration of drug—up to about 12 mM. The initial solution concentration obtainable depends, of course, on the selection of the particular metalloporphyrins to be formulated. The tin metalloporphyrin are generally more soluble than the zinc analogs and permit higher initial concentrations.

A stabilizer can optionally be added to the initially dissolved drug, or the initial solution can be first neutralized. It may be advantageous to add stabilizer before neutralization, as this may prevent problems with the drug reprecipitating from solution during neutralization. Suitable stabilizers are biocompatible proteins such as, for example, BSA or HSA. The stabilizer is added so as to result in a final concentration of 0.5-5% in the finished formulation.

The solution is then neutralized by titration with a suitable organic or inorganic acid to the pH range of 7.4-7.8, and may be further diluted. Suitable pharmaceutically acceptable organic acids are known in the art and include, for example, acetic acid, succinic acid, lactic acid, and citric acid. Suitable inorganic acids include hydrochloric, sulfuric, and phosphoric acids, all used in dilute solution. Hydrochloric acid is preferred. A concentration of approximately 0.5–1.5N is appropriate; the convenient concentration will depend on the amount of amine base used initially to dissolve the drug.

Depending on the metalloporphyrin chosen as the active ingredient, the impact of the method of formulation on ease of obtaining a stable preparation will vary. Many of the most desired forms of the drug, such as zinc mesoporphyrin or zinc protoporphyrin, are highly insoluble in aqueous base, and attempts to bring them into solution have been described as reminiscent of attempts to dissolve rock. The addition of the water-soluble organic amine to the initial solvent permits facile dissolution of even these refractory drugs.

In a typical preparation, 20–30 mg porphyrin, such as zinc or tin protoporphyrin is dissolved in 500 ul 10% (v/v) ethanolamine. The pH is slowly adjusted to 7.8 with 1N HCl (requiring approximately 1 ml) using a manual titrater with constant stirring. A constant flow rate of about 0.35 ml 1N HCl per minute is typical. The rate of neutralization must be monitored so that precipitation of the drug does not occur.

The nearly neutralized solution (pH is 7.8–7.4) is then diluted as desired. Even if not previously supplemented with stabilizer, the resulting preparation may be supplemented (or further supplemented) to obtain about 0.5–5%, preferably about 1%, stabilizer (or additional stabilizer), such as human or bovine serum albumin. Other suitable stabilizers may also be used.

The resulting formulations are stable when stored in the dark at low temperature for periods exceeding one month.

The final concentration of the drug in the formulation is of the range of 0.035–2%, preferably 0.035–1%. Because of varying solubilities of the forms of metalloporphyrins used, the upper limit may vary within this range. However, for most metalloporphyrins, at least a 1% concentration in the final preparation can be achieved. This permits the administration of 10 mg of drug (or about 14 umol) in only one ml of formulation.

The resulting composition can be administered at a dosage which is dependent on the choice of porphyrin drug. For use of zinc protoporphyrin, for example, as a chemopreventive agent, effective doses are typically in the range of 0.1–100 umol/kg, preferably less than 1 umol/kg. Typically, only a single treatment is given, but administration of this dosage at one dosage per day for 4–5 days can also be used. For the corresponding tin protoporphyrin, however, lower amounts should be used. A study involving formulations of this type which can be used to estimate dosage levels is found in Hamori, C. J., et al. *Research Commun Chem Pathol Pharmacol* (1988) 6241–48, cited above, and incorporated herein by reference. Descriptions of the use of alternate tin protoporphyrin and mesoporphyrin are described by Delaney, A., et al. *Pediatrics* (1988) 81:498–504; and by Drummond, G. S., et al., *Arch Biochem Biophys* (1987) 255:64–74.

The use of the water-soluble organic amines as bases in dissolving the various porphyrin derivatives is highly advantageous as the efficacy of the amine aqueous solutions as solvents is much greater than that of the mineral bases. For example, zinc mesoporphyrin will not dissolve in sodium hydroxide. It has been shown by Hamori, C. J. (supra) that the excipient amines do not affect dosage range.

We claim:

1. A solution useful in preparing a pharmaceutical composition for the treatment or prevention of jaundice, which solution comprises an effective amount of a metalloporphyrin consisting of at least one porphyrin-related tetrapyrrole nucleus metal chelate wherein the metal ion is selected from the group consisting of $Zn^{+2}$, $Sn^{+4}$, $Mn^{+2}$, $Ni^{+2}$ and $Cr^{+3}$, effective in the treatment of jaundice,
   dissolved in an aqueous 5–50% solution of an organic amine, said organic amine being a strong base.

2. A pharmaceutical composition which comprises the solution of claim 1 neutralized to a pH range of 7.4–7.8.

3. The solution of claim 1 which further includes at least one stabilizer.

4. The composition of claim 2 which further includes 0.5–5% stabilizer.

5. The solution of claim 1 wherein the metalloporphyrin is selected from the group consisting of zinc protoporphyrin and zinc mesoporphyrin.

6. The composition of claim 2 wherein the metalloporphyrin is selected from the group consisting of zinc protoporphyrin and zinc mesoporphyrin.

7. The solution of claim 1 wherein the amine is selected from the group consisting mono-, di- and triethylamine and mono-, di- and triethanolamine.

8. The solution of claim 7 wherein the amine is ethanolamine.

9. The composition of claim 2 wherein the amine is selected from the group consisting mono-, di- and triethylamine and mono-, di- and triethanolamine.

10. The composition of claim 9 wherein the amine is ethanolamine.

11. A method to prepare a composition suitable for the prevention or treatment of jaundice which method comprises:
   a) dissolving a metalloporphyrin consisting of at least one porphyrin-related tetrapyrrole nucleus metal chelate wherein the metal ion is selected from the group consisting of $Zn^{+2}$, $Sn^{+4}$, $Mn^{+2}$, $Ni^{+2}$ and $Cr^{+3}$, which is effective in treating jaundice,
   in an aqueous solution containing 5–50% of a water-soluble organic amine which amine is a strong base, effective to dissolve said metalloporphyrin and
   b) neutralizing the resulting solution by gradual addition of aqueous solution of acid.

12. The method of claim 11 which further includes the addition of stabilizer after step a) or step b).

13. The method of claim 11 wherein the organic amine is selected from the group consisting of mono-, di- and triethylamine and mono-, di- and triethanolamine.

14. The method of claim 13 wherein the amine is ethanolamine.

15. The method of claim 11 wherein the metalloporphyrin is selected from zinc protoporphyrin and zinc mesoporphyrin.

16. A method to prevent or treat jaundice in a human subject which method comprises administering to a subject in need of such prevention or treatment an effective amount of the composition of claim 2.

* * * * *

UNITED STATES PATENT AND TRADEMARK OFFICE

CERTIFICATE OF CORRECTION

PATENT NO. : 5,081,115

DATED : January 14, 1992

INVENTOR(S) : Hendrik J. Vreman, David K. Stevenson

It is certified that error appears in the above-identified patent and that said Letters Patent is hereby corrected as shown below:

Col. 1, line 8

--This invention was made with Government support under contract HD14426 awarded by the National Institutes of Health. The Government has certain rights in this invention.--

Signed and Sealed this

Fifteenth Day of August, 1995

Attest:

BRUCE LEHMAN

*Attesting Officer*

*Commissioner of Patents and Trademarks*